United States Patent [19]

Poncy et al.

[11] 4,275,812
[45] Jun. 30, 1981

[54] SURGICAL GLOVE PACKAGE AND DONNING METHOD

[76] Inventors: Mark P. Poncy; George W. Poncy; Richard P. Poncy, all of 3660 E. Indus. Way, Riviera Beach, Fla. 33404

[21] Appl. No.: 797,384

[22] Filed: May 16, 1977

Related U.S. Application Data

[63] Continuation of Ser. No. 618,336, Oct. 1, 1975, abandoned, and a continuation-in-part of Ser. No. 600,893, Aug. 1, 1975, Pat. No. 4,002,276.

[51] Int. Cl.³ ............................................. B65D 85/18
[52] U.S. Cl. ............................... 206/278; 2/161 R; 2/DIG. 7; 128/132 R; 206/438; 223/111
[58] Field of Search ................. 206/278, 438, 440; 2/16, 160, 161 R, 162, 168, DIG. 7, 270; 223/112, 111; 128/132 R, 132 D; 312/1; 15/227

[56] References Cited

U.S. PATENT DOCUMENTS

| | | | |
|---|---|---|---|
| 1,938,685 | 12/1933 | Breuls et al. | 223/111 |
| 1,996,377 | 4/1935 | Hinchen | 223/111 |
| 3,099,015 | 7/1963 | Renehan | 312/1 |
| 3,103,016 | 9/1963 | Perlman | 2/270 |
| 3,237,821 | 3/1966 | Hayne et al. | 223/111 |
| 3,323,846 | 6/1967 | Boddy | 312/1 |
| 3,337,279 | 8/1967 | Reinhardt et al. | 312/1 |
| 3,354,922 | 11/1967 | James | 146/215 |
| 3,476,109 | 11/1969 | Hurney | 128/157 |
| 3,811,132 | 5/1974 | Segonzac et al. | 2/270 |
| 4,069,913 | 1/1978 | Harrigan | 206/278 |

*Primary Examiner*—Herbert F. Ross
*Attorney, Agent, or Firm*—Lane, Aitken, Ziems, Kice & Kananen

[57] ABSTRACT

In a surgical glove package, the surgical glove is contained in a cylindrical ring with the cuff of the glove stretched around the ring to open the cuff of the glove. A bag also contained within the ring has its mouth sealed around said ring and encloses the outer surface of the glove to protect the sterility thereof. To don the glove, the hand is inserted through the ring into the glove and then the cuff of the glove is released from the ring. The ring is then removed from the hand in a manner to turn the bag inside out as the ring passes over the hand so that the bag remains between the ring and the hand as the ring is passing over the hand.

11 Claims, 8 Drawing Figures

FIG. 6.
FIG. 7.
FIG. 8.
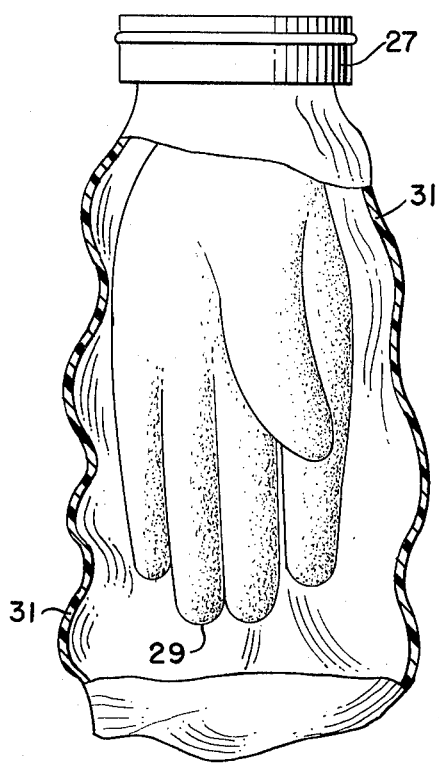
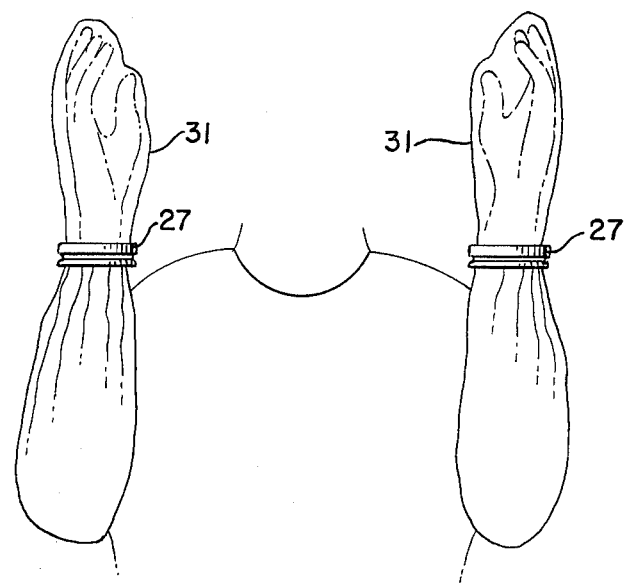
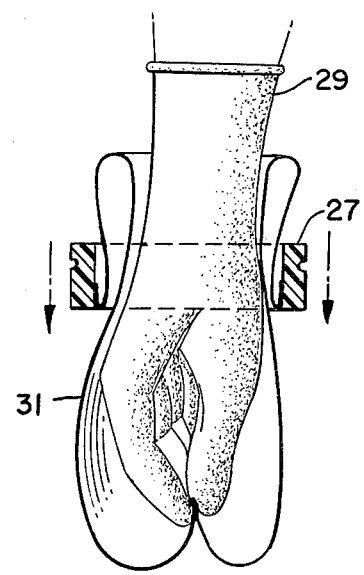

SURGICAL GLOVE PACKAGE AND DONNING METHOD

CROSS-REFERENCE TO RELATED APPLICATIONS

This is a continuation, of application Ser. No. 618,336 filed Oct. 1, 1975, now abandoned, and a continuation-in-part of application Ser. No. 600,893 entitled "SURGICAL GLOVE DONNING SYSTEM" filed Aug. 1, 1975, now U.S. Pat. No. 4,002,276.

BACKGROUND OF THE INVENTION

This invention relates to a surgical glove package designed to facilitate donning of this surgical glove package therein and to a method of donning surgical gloves.

The technique now used for donning surgical gloves require that the sealed package containing sterile gloves be carefully opened so that the inner surfaces of the package, and more particularly, the outside surfaces of the gloves contained therein, do not come in contact with any surface. Upon being opened, the gloves are positioned next to each other with the large part of the cuff portions of the gloves being turned on themselves or inside out. An assistant grasps one glove by the folded cuff portion so as to touch only that surface when the glove is donned. The touched surface will thus correspond only to the glove's inner surface. After removing the glove from the package, the assistant grasps the cuff portion of the glove with the fingers of both hands and stretches the opening as much as possible in order to enlarge the cuff opening. The glove is then held in a somewhat vertical position in order to present the glove opening to the surgeon's hand. Care must be taken to make sure that the drooping glove fingers do not touch any surface other than the adjacent outer glove surfaces. The surgeon then vigorously thrusts his hand into the enlarged glove opening in an attempt to gain full entry into the fingers of the glove. The assistant must maintain a firm grip on the glove cuff portion in order to provide the resistance to the thrust necessary for the surgeon's hand to gain access to the fingertips of the glove. At the precise moment the surgeon's hand reaches the fingertips, the assistant must release hold of the glove to permit the cuff portion to snap tightly around the surgeon's wrist. The same procedure is followed for donning the second glove.

Obviously this procedure is fraught with accidental contamination possibilities, especially during times of distress and urgency as may exist when torn gloves have to be replaced during an operation. In addition, this technique requires assistance of a second person with the necessary skill. Moreover, because of the difficulty in fully inserting the hand into the glove, the inner surfaces of the glove must be heavily powdered to lubricate the glove surface relative to the surgeon's hand. The powdering operation normally results in powder getting on the external surfaces of the glove. As a result, the surgeon must use sterile wipes to cleanse the glove surfaces of powder because the presence of powder particles in the surgical wound would aggravate internal organs and tissue and would adversely affect healing following surgery.

In the instances where the user of surgical gloves does not have any assistance, care must be taken to avoid touching the outer surface to avoid contamination. This is difficult to do since the wearer must also stretch the glove enough to provide access with one hand while inserting the other.

SUMMARY OF THE INVENTION

In the above identified copending application Ser. No. 600,893, a surgical glove package and apparatus designed to overcome these problems is disclosed. The package comprises a cylindrical ring made of paperboard or plastic with the cuff of the glove stretched around the edge of the ring to the outside surface thereof. A bag has its mouth fixed to the ring so that the bag encloses the outer surface of the glove to protect the sterility of the outer surface of the glove. The apparatus of the above identified parent application operates to inflate the glove in a manner so that the surgeon can insert his hand into the glove while inflated thus making it very easy for the surgeon to don the glove without assistance.

The present invention provides another method of donning a glove making use of the same glove package but without the need of the glove inflating apparatus disclosed in the copending application.

In accordance with the present invention, the surgeon dons surgical gloves by inserting his hand into the uninflated gloves through the rings of the glove packages while the cuffs of the gloves are stretched around the package rings. Because the rings hold the gloves open, the surgeon can insert his hands into the gloves without assistance and much more easily than can be done with the glove packages of the prior art. When the surgeon inserts his hands into the gloves, the bags of the glove packages will still be covering the outside surface of the gloves enabling the gloved hand of the surgeon to handle or manipulate the glove package for the other hand through the covering bag. After both hands have been encased with the glove, the surgeon releases the cuff of each glove from the ring by manipulating the cuff with his finger of his other hand through the covering bag. The rings and covering bags are then removed in a manner so that the bag turns inside out as the ring passes over the surgeon's gloved hand. In this manner, the bag prevents the ring from coming into direct contact with the outside surface of the glove as the ring passes over the surgeon's hand and thus protects the sterility of the outside surface of the glove from the ring, which might have become contaminated from contact with the surgeon's wrist or sleeve.

The present invention thus provides a much easier technique for the surgeon to don surgical gloves without assistance than was possible with prior art glove packages. The present invention also provides a convenient surgeon's glove package, which not only facilitates the donning of the glove but also serves as a convenient means for shipping and storing the sterile gloves.

Further objects and advantages of the present invention will become readily apparent as the following detailed description of the invention unfolds and when taken in conjunction with the drawings identified below.

BRIEF DESCRIPTION OF THE DRAWINGS

FIG. 6 is a view of the glove package of FIGS. 1-3 with the contents of the package allowed to hang distended from the ring of the package ready for donning by the surgeon; and FIGS. 7 and 8 illustrate steps in the method of donning surgical gloves of the present invention.

DESCRIPTION OF THE PREFERRED EMBODIMENTS

Figure 1:
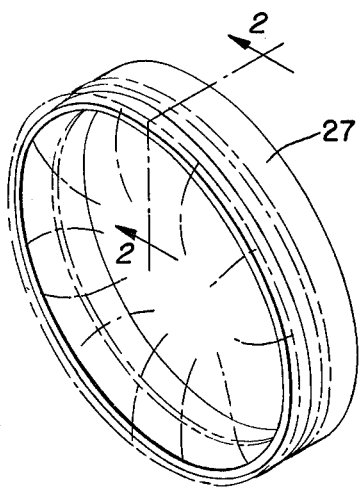
FIG. 1 is a perspective view of one embodiment of the surgical glove package of the invention with the outer wrapping of the package removed.
Figure 2:
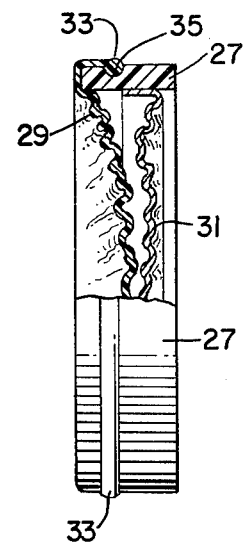
FIG. 2 is a partial sectional view taken along the lines 2—2 of FIG. 1 illustrating the surgical glove package in elevation.

The embodiment of the surgical glove package as shown in FIGS. 1 and 2 comprises a ring 27, which may be made of paperboard or may be molded from a rigid plastic such as styrene or high density polyethylene. A conventional surgical glove 29, which is made of a thin, impervious, elastomeric material is removably mounted on the ring 27 together with a thin, flexible, impervious, transparent bag 31 covering the outer surface of the glove 29. The mouth of the bag 31 is sealed to the ring 27 so that the bag 31 completely encloses the outer surfaces of the glove 29. As shown in FIGS. 1 and 2, the outer surfaces of the mouth of the bag 31 are sealed to the inner cylindrical wall of the ring 27. However, the bag 31 may be secured to the ring 27 by sealing the inner surfaces of the mouth of the bag to the outer surface of the ring 27. The bag 31 may be made from very thin, flexible, plastic film.

The embodiment of the package shown in FIGS. 1 and 2 is designed for gloves provided with a bead at the end of the cuff portion of the surgical glove. The cuff of the surgical glove is stretched around the end wall of the ring and the bead of the glove designated by the reference number 33 fits in a circular groove 35 extending around the cylindrical wall of the ring 27. Since the cuff of the glove 29 is stretched around the end of the ring 27, it fits tightly against the ring 27 so that the bag 31 sealed around the ring 27 completely encloses the outer surface of the glove 29 and protects the sterility thereof.

Figure 3:
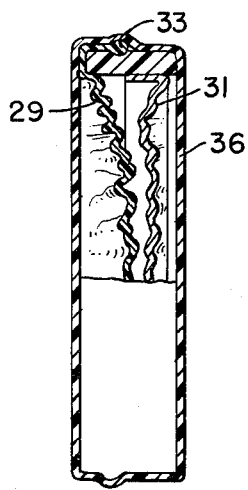
FIG. 3 is an illustration of the surgical glove package of FIGS. 1 and 2 with its outer wrapping.

The glove 29 and the sleeve 31 are folded up within the cylinder defined by the walls of the ring 27 so as to provide a compact, convenient package for storage and transportation. The package is sealed with appropriate outer wrapping 36 as shown in FIG. 3 and the gloves thus packaged are provided with suitable identification "right" and "left." The contents of the sealed package are sterilized with ethylene oxide gas in the conventional manner as well known in the art. It will be recognized that the wrapping 36 is not necessary to protect the sterility of the outer surface of the glove, as this function is performed by the bag 31. Nevertheless, as an added precaution, it is desirable to keep the inner surface of the glove and the outer surface of the bag sterile during shipment and storage and the wrapping 36 performs this function.

Figure 4:
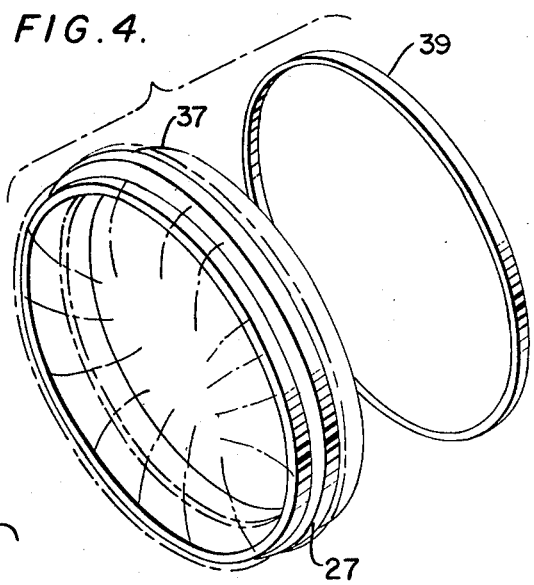
FIG. 4 is an exploded perspective view of another embodiment of the surgical glove package of the invention with the outer wrapping of the glove removed.
Figure 5:
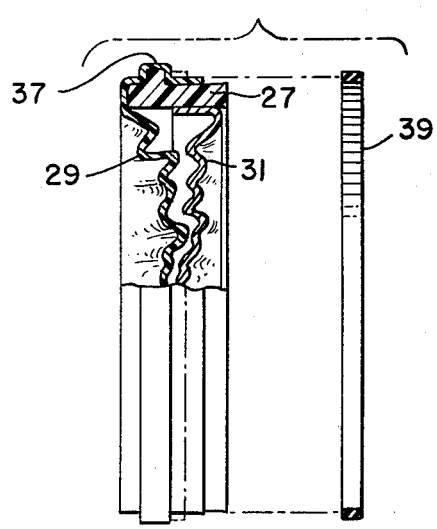
FIG. 5 is a partial sectional view taken along the lines 5—5 of FIG. 4 showing the glove package of FIG. 4 in elevation.

The alternative embodiment of the ring package illustrated in FIGS. 4 and 5 is designed for use with gloves which do not have a bead at the cuff end of the glove. In this embodiment, the ring is provided with a ridge 37 extending around the outer surface of the ring 27 and the cuff of the glove 29 is stretched around the end of the ring and over the ridge 37. An elastic band 39, such as a conventional rubber band, is provided to secure the cuff end of the glove to the ring 27. The rubber band is positioned around the cuff portion of the glove against the shoulder defined by the ring 37 on the opposite side thereof from the end of the ring 27 around which the cuff portion of the glove 29 is stretched.

In accordance with the glove donning method of the present invention, the surgeon would remove the wrapping 36 from a glove package for the glove for each hand. The wrappings are removed after laying the packages flat on a horizontal working surface with the inner surface of the glove presented facing upward. Then, assuming that the left glove is to be donned first, the surgeon grasps the ring 27 containing the left glove with his right hand and positions the plane of the ring horizontally so that the glove 29 and the bag 31 are allowed to hang in a distended position from the ring as shown in FIG. 6. The surgeon then inserts his left hand through the ring 27 fully into the glove 29 while holding the ring 27 with his right hand. Because the ring 27 holds the mouth of the glove 29 in an open position, the surgeon can insert his hand fully into the glove without assistance and with much less difficulty than was possible in the prior art glove packages. Also, at this time, the outer surface of the glove 29 will still be completely enclosed by the bag 31 so in this operation the surgeon does not need to take care to avoid touching any surface with the outside surface of the glove as he is donning the glove. After the surgeon has fully inserted his left hand into the glove, he then picks up the ring 27 of the glove package for his right hand with his left hand through the bag 31 covering the gloved left hand and holds the ring in a horizontal position so that the glove and bag will hang in a distended position as in the illustration of FIG. 6. The surgeon then inserts his right hand through the ring fully into the glove while holding the ring with his left hand so that both hands will then by fully encased by the surgeon's gloves. Because the ring being grasped by the gloved left hand is grasped through the bag 31 covering his left hand, there is no danger of contamination of the glove on the left hand. After both hands have been inserted into the gloves in this manner, the surgeon releases the cuff of the glove on his left hand from the ring 27 by manipulating the point at which the cuff is held on the outside of the ring with the fingers of his right hand through the bag which will at this time be still covering the outer surface of the glove encasing the right hand. In the cause of a glove package in which the surgeon's glove has a bead, such as illustrated in FIGS. 1-3, the surgeon releases the cuff of the glove by rolling the bead 33 out of the groove 35. All the surgeon need do is merely start the rolling operation enough to remove the bead partially from the groove and the cuff of the glove will come loose from the ring and snap around the surgeon's wrist because of the stretched condition of the cuff on the ring. After releasing the cuff of his glove on his left hand in this manner, the surgeon will then release the cuff of the glove on his right hand in this same manner by using the fingers of his left hand through the bag which at this time will still be positioned over the surgeon's gloved left hand.

At this time both hands will be gloved and the bags 31 will still be over the gloved hands. The rings 27 attached to the bags will be over the surgeon's wrists and no longer attached to the cuffs of the glove. Until the surgeon is ready to remove the bags 31 from the covering position, he must hold his hands in either a horizontal position or raised position, such as shown in FIG. 7, so as to maintain the bags 31 in the covering position. At this time, the surgeon can still touch non-sterile surfaces through the bags 31 covering the gloves without contaminating the surfaces of the gloves. When the surgeon is ready to remove a bag 31 and ring 27 from a gloved hand, he positions his hand to extend vertically downward and removes the ring. As the ring comes over the surgeon's hand, it will turn the bag 31 inside out as illustrated in FIG. 8 so that the bag 31 stays between the ring 27 and the gloved hand and the inside surface of the ring 27, which may have become contaminated through contact with the surgeon's wrist or sleeve, cannot come into contact with the outer surface of the glove. The bag turns inside out as the ring is removed because the flexibility and lightness of the bag causes it to exhibit a parachute effect as the ring comes off of the hand.

The preferred procedure is for the surgeon to remove the bags 31 one at a time. To remove the first bag from his left hand, for example, the surgeon grasps the inside of the bag with his gloved left had as shown in FIG. 8 and then pulls the ring 27 down over the left hand while holding the ring with his right hand through the bag still covering his right hand. Then to remove the bag and ring from his right hand, the surgeon grasps the inside of the bag covering the right hand with his right hand and grasps the ring on his right wrist with his left hand. To protect the sterility of the gloved left hand from contamination by the ring on the wrist of the right hand, the surgeon interposes the bag 31 which formerly covered his left hand between the ring on the right wrist and his gloved left hand and grasps the ring through the bag. This operation of interposing the bag, which formerly covered his left hand, between his gloved left hand and the ring on his right wrist can be readily accomplished without danger of contamination by the surgeon maintaining the grasp of his left hand on the inner surface of the bag from the time when the bag and ring were being removed from his left hand. Because at this time the bag which formerly was on the left hand will be turned inside out, the gloved left hand will touch only the sterile inner surface of the bag when the surgeon grasps the ring on the right wrist through the bag. The surgeon then removes the ring from the right hand causing the bag to turn inside out as the ring is removed.

An alternative method of removing the bags 31 from the gloved hands is for the surgeon to grasp each of the bags from the inside with both hands and then to invert his hands and shake the rings off. The parachute effect resulting from lightness and flexibility of the bags will cause the bags to turn inside out as the rings pass over the surgeon's hands thus protecting the sterility of the outer surface of the glove from possible contamination by the inner surface of the ring.

Thus it will be appreciated that the present invention provides an improved surgical glove package and method of donning surgical gloves which make it possible to don surgical gloves without assistance and without danger of contaminating the outer surface of the glove much more easily than can be accomplished with the glove packages of the prior art. The above description is of the preferred embodiments of the invention and many modifications may be made thereto without departing from the spirit and scope of the invention which is defined in the appended claims.

We claim:

1. A surgical glove package comprising a ring and a glove made of elastomeric material having a sterile outer surface and having the cuff portion thereof stretched around the edge of said ring to the outside surface of said ring, said ring having an axial dimension shorter than the length of said glove from the cuff thereof to the fingertips thereof, said glove being extendable to an unfolded condition, said ring being unattached to any inflexible apparatus surrounding the outside surface of said glove when said glove is extended to said unfolded condition, said package including means enabling the cuff of said glove to be released from said ring onto the wrist of an inserted hand by manual manipulation of the cuff solely by the fingers of the opposite hand of the person donning the glove.

2. A flexible glove package as recited in claim 1 wherein the cuff end of said glove is formed into a bead, the outer surface of said ring having an annular groove defined therein, said bead being positioned in said groove.

3. A glove package as recited in claim 1 wherein an annular ridge is formed on the outer cylindrical surface of said ring and said cuff portion extends over said ridge and is held in position by an elastic band separate from said glove extending around the cuff portion of said glove holding said cuff portion against the outer surface of said ring adjacent to said ridge on the opposite side thereof from the edge of said ring around which said cuff portion is stretched.

4. A surgical glove package comprising a ring and a glove made of elastomeric material having a sterile outer surface and having the cuff portion thereof stretched around the edge of said ring to the outside surface of said ring, said ring having an axial dimension shorter than the length of said glove from the cuff thereof to the fingertips thereof, said glove being extendable to an unfolded condition, said ring being unattached to any inflexible apparatus surrounding the outside surface of said glove when said glove is extended to said unfolded condition, and means to retain all of the material of said glove except for said cuff portion within the cylinder formed by said ring.

5. A glove package as recited in claim 4 wherein said means to retain all of the material of said glove except for said cuff portion comprises packaging materials enclosing said glove within said ring, the surfaces of said glove being sterile within said packaging materials.

6. A flexible glove package comprising a ring and a glove made of elastomeric material having a sterile outer surface and having the cuff portion thereof stretched around the edge of said ring to the outside surface of said ring, said ring having an axial dimension shorter than the length of said glove from the cuff thereof to the fingertips thereof, said glove being extendable to an unfolded condition, said ring being unattached to any inflexible apparatus surrounding the outside surface of said glove when said glove is extended to said unfolded condition, a tubular member made of flexible impervious material and fixed to said ring around the circumference of said ring, said tubular member covering the outer surface of said glove, said tubular member being sufficiently large to cover said glove when a hand has been inserted fully into said glove, and means to retain all of the material of said glove except for said cuff portion and at least the lower portion of said tubular member within the cylinder formed by said ring.

7. A glove package as recited in claim 6 wherein said means to retain all of the material of said glove except said cuff portion comprises packaging material enclosing said glove and said tubular member within said ring.

8. A glove package comprising a ring and a glove made of elastomeric material having a sterile outer surface and having the cuff portion thereof stretched around the edge of said ring to the outside surface of said ring, said ring having an axial dimension shorter than the length of said glove from the cuff thereof to the fingertips thereof, said glove being extendable to an unfolded condition, said ring being unattached to any inflexible apparatus surrounding the outside surface of said glove when said glove is extended to said unfolded condition, and a tubular member made of flexible impervious material and fixed to said ring around the circumference of said ring, said tubular member covering the outer surface of said glove, said tubular member being sufficiently large to cover said glove when a hand has been inserted fully into said glove, the opposite end from said one end of said tubular member being closed to form a bag surrounding the outside surface of said glove.

9. A glove package comprising a glove made of elastomeric material having a sterile outer surface, a tubular member made of flexible impervious material covering the outer surface of said glove, and means to releasably attach the periphery of one end of said tubular member to the periphery of said cuff, said tubular member being sufficiently large to cover the outside surface of said glove when a hand is inserted fully into said glove, the opposite end of said tubular member from the end releasably attached to said cuff being closed to form a bag surrounding the outside surface of said glove.

10. A method of donning a surgical glove having its cuff stretched around the axial end of a packaging ring with a bag having its mouth sealed to said ring to enclose the outer surface of said glove comprising the steps of inserting the hand through said ring into said glove, then releasing said cuff portion of said glove from said ring and onto the wrist of said hand, and then passing said ring over said hand while turning said bag inside out so as to maintain said bag between said ring and said hand as said ring passes over said hand.

11. A method of donning a surgical glove having its cuff stretched around the axial end of a packaging ring comprising the steps of inserting the hand through said ring into said glove while said glove is uninflated and then releasing the cuff portion of said glove from said ring onto the wrist of said hand.

* * * * *